United States Patent
Liu

(10) Patent No.: US 12,257,260 B2
(45) Date of Patent: Mar. 25, 2025

(54) PHARMACEUTICAL USE OF ANEMOSIDE B4 AGAINST ACUTE GOUTY ARTHRITIS

(71) Applicant: Qi Liu, Beijing (CN)

(72) Inventor: Qi Liu, Beijing (CN)

( * ) Notice: Subject to any disclaimer, the term of this patent is extended or adjusted under 35 U.S.C. 154(b) by 1011 days.

(21) Appl. No.: 17/286,803

(22) PCT Filed: Dec. 21, 2018

(86) PCT No.: PCT/CN2018/122655
§ 371 (c)(1),
(2) Date: Apr. 19, 2021

(87) PCT Pub. No.: WO2020/077819
PCT Pub. Date: Apr. 23, 2020

(65) Prior Publication Data
US 2021/0338700 A1    Nov. 4, 2021

(30) Foreign Application Priority Data

Oct. 18, 2018 (CN) .......................... 201811214694.3

(51) Int. Cl.
*A61K 31/704* (2006.01)
*A61K 9/00* (2006.01)
*A61P 19/02* (2006.01)

(52) U.S. Cl.
CPC .......... *A61K 31/704* (2013.01); *A61K 9/0019* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 11,351,184 B2* | 6/2022 | Liu | A61K 47/26 |
| 2004/0058918 A1* | 3/2004 | Dominguez | A61P 1/18 |
| | | | 548/366.1 |
| 2007/0161559 A1* | 7/2007 | Petrilli | A61K 31/395 |
| | | | 514/420 |
| 2018/0228778 A1* | 8/2018 | Gill | A61P 11/02 |

FOREIGN PATENT DOCUMENTS

| | | | | |
|---|---|---|---|---|
| CN | 101822659 A | * | 9/2010 | ........... A61K 31/165 |
| CN | 105213410 A | * | 1/2016 | ........... A61K 31/704 |
| CN | 105535004 A | | 5/2016 | |
| CN | 107137413 A | * | 9/2017 | ........... A61K 31/704 |
| JP | 2006213657 A | | 8/2006 | |

OTHER PUBLICATIONS

Hu, Y., Chen, X., Duan, H., Hu, Y., & Mu, X. (2009). Pulsatilla decoction and its active ingredients inhibit secretion of No., ET-1, TNF-α, and IL-1α in LPS-induced rat intestinal microvascular endothelial cells. Cell Biochemistry and Function., 27(5), 284-288. (Year: 2009).*

Lyu, S., Ding, R., Liu, P., OuYang, H., Feng, Y., Rao, Y., & Yang, S. (2019). LC-MS analysis of serum for the metabolomic investigation of the effects of pulchinenoside b4 administration in monosodium urate crystal-induced gouty arthritis rat model. Molecules, 24(17), 3161. (Year: 2019).*

Yuan, Shan et al.; "Clinical Experience of Flower Bud of Pulsatilla in Treating Gouty Arthritis"; Journal of Clinical Medical, vol. 2, No. 23, Aug., 2015, pp. 4911 and 4914.

* cited by examiner

*Primary Examiner* — Dale R Miller
(74) *Attorney, Agent, or Firm* — NKL Law; Allen Xue

(57) ABSTRACT

Use of anemoside B4 in the preparation of a medicament for treating acute gouty arthritis.

10 Claims, No Drawings

PHARMACEUTICAL USE OF ANEMOSIDE B4 AGAINST ACUTE GOUTY ARTHRITIS

CROSS-REFERENCES TO RELATED APPLICATIONS

This application is a U.S. national phrase entry of PCT International Application No. PCT/CN2018/122655, filed Dec. 21, 2018, which claims the benefit of Chinese application No. 201811214694.3 filed Oct. 18, 2018 and entitled "Medical use of anemoside B4 against acute gouty arthritis", which is herein incorporated by reference in its entirety.

TECHNICAL FIELD

The present invention belongs to the field of medicine, and particularly relates to a new medical use of anemoside B4.

BACKGROUND ART

Gout is a group of diseases in which long-term purine metabolism disorders and increased blood uric acid cause tissue damage. Acute gouty arthritis is a typical symptom of gout, as a characteristic acute inflammatory reaction caused by the deposition of urate crystals on the joints (especially the ankle and foot joints) and the surrounding connective tissue. It often attacks at night, and the patient can wake up from pain and cannot fall asleep all night. Acute gouty arthritis often recurs, and over time, it can develop into polyarthritis or migratory arthritis. The affected joints are red, swollen, hot, painful, and restricted in movement, which seriously affects the life quality of patients. In China, with the continuous improvement of people's living standards, due to much intake of high-purine, high-protein, and high-fat foods, the incidence of gout has not only increased rapidly, but the age of the disease has gradually decreased, and teenage patients with gout have appeared. It is predicted that in the next 10 years, gout will become a metabolic disease second only to diabetes in China.

At present, for the treatment of acute gouty arthritis, the commonly used drugs are non-steroidal anti-inflammatory drugs (such as diclofenac sodium, etc.), colchicine, and glucocorticoids. Although these drugs have achieved certain clinical effects, the accompanying side effects and adverse reactions are inevitable, such as the gastrointestinal reactions of traditional non-steroidal anti-inflammatory drugs; the adverse reactions of COX-2 inhibitors in cardiovascular system; bone marrow suppression, liver damage, allergies, and neurotoxicity of colchicine; "rebound" of glucocorticoids, etc. Therefore, exploring new drugs for the treatment of acute gouty arthritis has become a hot spot in the medical field.

The traditional Chinese medicine Radix Pulsatillae is the dried root of *Pulsatilla chinensis* (Bge.) Regel, belonging to the genus *Pulsatilla* in the Ranunculaceae family, and was first published in "Shen Nong's Materia Medica". Its nature and taste are bitter and cold, and it has the effects of clearing away heat and detoxifying, cooling blood to stop diarrhea, drying dampness and killing insects, etc. It is used to treat heat toxins and blood dysentery, warm malaria, cold and heat, epistaxis, and blood hemorrhoids. Through modern pharmacological research, it has been found that Radix Pulsatillae has more diverse activities, such as broad-spectrum antibacterial effects, anti-tumor, anti-inflammatory, immune function enhancement and so on.

Radix Pulsatillae has rich triterpene saponins, and anemoside B4 belongs to the pentacyclic triterpene saponins of lupine-type, with the structural formula of 1.

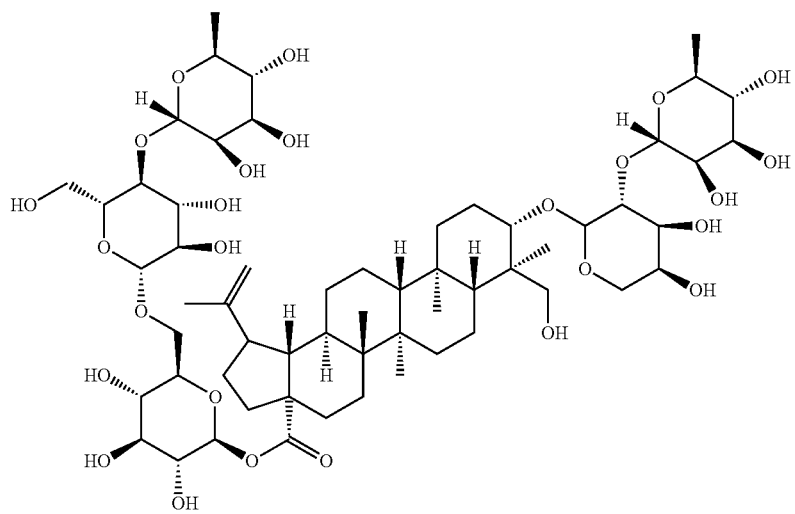

Anemoside B4 has strong activity, such as the Chinese invention patent application with publication number CN105213410 A (publication date Jan. 6, 2016) discloses the use of anemoside B4 as an immunomodulator in the drugs for treatment of acute inflammation. The inflammation includes acute kidney injury, acute liver injury and acute lung injury caused by overexpression of inflammatory factors. Another example is the Chinese invention patent application with publication number CN105535004 A (published on May 4, 2016), which discloses the use of the compound as an EV71 virus inhibitor in the preparation of drugs against hand, foot and mouth disease. But so far, there is no report on the use of anemoside B4 for the treatment of acute gouty arthritis.

CONTENT OF THE INVENTION

Aiming at the deficiencies of the prior art, the present invention provides a new medical use of anemoside B4 in the treatment of acute gouty arthritis.

In order to achieve the above technical effects, the present invention adopts the following technical solutions:

The use of anemoside B4 in the preparation of drugs for treatment of acute gouty arthritis.

As a preferable embodiment, the present invention provides the use of anemoside B4 as the sole active ingredient in the preparation of drugs for treatment of acute gouty arthritis.

As another preferable embodiment, the present invention provides the use of anemoside B4 and other active ingredients in the preparation of drugs for treatment of acute gouty arthritis, wherein the other active ingredients are selected from one or more of non-steroidal anti-inflammatory drugs, colchicine, and glucocorticoids.

Said non-steroidal anti-inflammatory drug includes but is not limited to ibuprofen, indomethacin, nimesulide, naproxen, nabumetone, diclofenac sodium, loxoprofen sodium, rofecoxib, celecoxib, etoricoxib, and so on.

Said glucocorticoid includes but is not limited to prednisone, meprednisone, betamethasone, beclomethasone dipropionate, diprospan, prednisolone, hydrocortisone, and dexamethasone.

Preferably, the drug also includes pharmaceutically acceptable excipients.

Preferably, the drug is selected from one or more of oral preparations and non-oral preparations.

Preferably, said non-oral preparation is selected from one or more of injections, preparations for rectal administration, and preparations for pulmonary administration, and more preferably, is selected from one or more of injections and preparations for rectal administration.

Said injection is selected from one or more of subcutaneous injections, intramuscular injections and intravenous infusions;

The formulation for rectal administration is selected from rectal suppositories and/or rectal infusions.

The pharmaceutically acceptable excipients of the present invention include but are not limited to (1) diluents, such as starch, powdered sugar, dextrin, lactose, pregelatinized starch, microcrystalline fibers, inorganic calcium salts (such as calcium sulfate, calcium hydrogen phosphate, medicinal calcium carbonate, etc.), mannitol, vegetable oil, polyethylene glycol, cocoa butter, semi-synthetic or fully synthetic fatty acid glycerides, glycerin gelatin, etc.; (2) binders, such as distilled water, ethanol, starch slurry, povidone, sodium carboxymethyl cellulose, hydroxypropyl cellulose, methyl cellulose and ethyl cellulose, hypromellose, etc.; (3) disintegrants, such as dry starch, sodium carboxymethyl starch, low-substituted hydroxypropyl cellulose, cross-linked polyvinylpyrrolidone, croscarmellose sodium, crospovidone, etc.; (4) lubricants, such as magnesium stearate, micronized silica gel, talc, hydrogenated vegetable oil, polyethylene glycols, magnesium laurylsulfate, etc.; (5) solvents, such as water for injection, ethanol, etc.; (6) preservatives, such as benzoic acid and its salts, sorbic acid and its salts, parabens, etc.

Preferably, the suitable individual is a mammal, and preferably a human.

For human subjects, the administration amount of anemoside B4 is usually 0.4-1.6 mg/kg body weight per day for adults (with body weight of 70 kg), and more preferably 0.4-1.6 mg/kg body weight in total once or several times a day.

The present invention further provides a method for treatment of acute gouty arthritis, that includes the step of administering anemoside B4 to a patient in need.

Preferably, the method, used for treatment of acute gouty arthritis, includes the step of administering anemoside B4 to a patient in need by subcutaneous injection, intramuscular injection, or intravenous infusion.

Preferably, the patient in need is a mammal, and more preferably a human.

Preferably, the method for treatment of acute gouty arthritis includes the step of administering anemoside B4 at a dose of 0.4-1.6 mg/kg body weight to a person in need once or several times a day.

As a preferable embodiment, the present invention provides a method of treating acute gouty arthritis, that includes the step of administering anemoside B4 at a dose of 0.4-1.6 mg/kg body weight to a person in need once or several times a day by subcutaneous injection, intramuscular injection or intravenous injection.

The present inventors have proved by multiple animal experiments that intravenous, subcutaneous or intramuscular injection of anemoside B4 can significantly alleviate joint swelling caused by acute gouty arthritis. Therefore, the injection of anemoside B4 is expected to provide a new choice for clinical treatment of acute gouty arthritis.

BEST MODE FOR CARRYING OUT THE INVENTION

Hereinafter, the present invention will be illustrated with reference to specific examples. Those skilled in the art can understand that these examples are only used to illustrate the present invention, and they do not limit the scope of the present invention in any way.

The experimental methods in the following examples, unless otherwise specified, are all conventional methods. The starting materials, reagents, materials, etc., used in the following examples, are all commercially available products unless otherwise specified.

Example 1

Preliminary Investigation on the Effect of Anemoside B4 on Sodium Urate-Induced Acute Gouty Arthritis in Rats 1. Experimental Materials 1.1 Test drugs: Anemoside B4 injection (homemade, hereinafter referred as "B4 injection"); colchicine, batch number: 171116, Xishuangbanna Banna Pharmaceutical Co., Ltd.

The above-mentioned B4 injection was prepared by the following method:

The pre-determined amount of anemoside B4 raw material was accurately weighed, to which was then added suitable amount of water for injection, and after anemoside B4 raw material was completely dissolved under magnetic stirring, activated carbon was added to the solution at 0.10% of the solution mass. The mixture was heated in 100° C. water bath and stirred for 15 min, then diluted to 100 ml with water for injection. The resultant solution was shaken well, and filtered through 0.22 μm microporous membrane to remove the activated carbon. 2 ml intermediate liquid was accurately measured and moved into a 5 ml ampoule, followed by sterilization at 115° C. for 30 min, to obtain the B4 injection.

1.2 Reagent: sodium urate, Sigma company; article number: U2875-5G; batch number: BCBS7438

1.3 Animals: 60 SD rats, male, 180-220 g, purchased from Hunan SJA Laboratory Animal Co., Ltd., used for experiments after one week of adaptive feeding.

1.4 Instrument: Toes Volume Measuring Instrument, Model: YLS-7B, Huaibei Zhenghua Biological Instrument Equipment Co., Ltd.

2. Experimental Method 2.1 Preparation of sodium urate (MSU) crystals and suspension: 5 ml of 1 mol/L NaOH solution and 800 mg sodium urate were added to 155 ml depyrogenated sterile water for injection and heated to boiling. Sodium urate was completely dissolved and then cooled down naturally under stirring. After that, 1 mol/L HCl was dropped to pH 7.0, then the solution became milky white, and was immediately centrifuged at 3000 r/min for 2 min. The crystals were collected, dried in an oven at 60° C., placed in an EP tube, and stored at 4° C. Prior to use, MSU crystals were autoclaved at 121° C. for 30 min, and dispersed in PBS to make the required concentration, i.e. to obtain a suspension of sodium urate (MSU). The film preparation of the suspension was performed, and the long fusiform crystals can be seen under the optical microscope.

2.2 Grouping, administration, and model establishment: 60 rats were randomly divided into 6 groups according to their body weights, 10 rats for each group: (1) model group; (2) colchicine group (0.3 mg/kg); (3) B4 subcutaneous injection group (5 mg/kg*2); (4) B4 intravenous injection group (5 mg/kg*2); (5) B4 intramuscular injection high-dose group (5 mg/kg*2); (6) B4 intramuscular injection low-dose group (2.5 mg/kg*2); normal group (5 rats). The normal group and the model group were injected with the same volume of normal saline, and each of B4 groups was given corresponding drugs by the corresponding route of administration for 3 days, twice a day, with an interval of 4 hours between two times.

Modeling method: on the day of modeling, the model was initially established 1 h after administrating in the drug groups. Among them:

(1) Model group: each rat was injected with 40 mg/mL MSU suspension to the back of the right ankle joint at a dose of 0.2 mL/rat;

(2) Colchicine group: the colchicine group was administered once on the day of modeling, and 1 h after administration, each rat was injected with 40 mg/mL MSU suspension on the dorsal side of the right ankle joint at a dose of 0.2 mL/mouse;

(3)-(6) B4 groups: 1 h after the last administration, each rat was injected with 40 mg/mL MSU suspension on the dorsal side of the right ankle joint at 0.2 mL/mouse, and 3 h after modeling, each test group was further administrated once.

2.3 Measurement of joint swelling: before modeling and 2 h, 4 h, 6 h, 8 h, 12 h, 24 h after modeling, the volume of the right ankle joint was measured, and the swelling degree was calculated by "joint volume after modeling-joint volume before modeling".

3. Experimental results

See Table 1.

The data in Table 1 showed that compared with the normal group, the joints of rats in the model group were significantly swollen 2 h after modeling, reached a peak 8 h-12 h after modeling, and decreased spontaneously 24 h after modeling. Compared with the model group, the joint swelling degree of each administration group was reduced to different degrees. Among them, 2-6 h after modelling in B4 subcutaneous injection group, 2-4 h after modelling in B4 intramuscular injection group, and 4-6 h after modelling in B4 intravenous injection group, and 4 h after modelling in the colchicine group, the swelling degree of the joints was significantly reduced, with significant differences. There was no significant difference between B4 groups and colchicine group, indicating that using the administration route and dosage in the experiment, the effect of B4 on reducing the acute joint swelling caused by sodium urate (MSU) crystals in rats was equivalent to that of colchicine.

4. Experimental conclusion

The results of this experiment showed that B4 could significantly alleviate the joint swelling of acute gouty arthritis by subcutaneous injection, intramuscular injection and intravenous injection.

Example 2

Further Investigation on the Effect of Anemoside B4 on Sodium Urate-Induced Acute Gouty Arthritis in Rats Based on Example 1, the dosage of anemoside B4 was reduced, and the effect on alleviating the joint swelling of acute gouty arthritis caused by sodium urate in rats was further investigated.

1. Experimental materials: same as item "1." in example 1.

2. Experimental method 2.1 Preparation of sodium urate (MSU) crystals and suspension: same as item "2.1" in Example 1.

2.2. Grouping, administration, and model establishment:

2.2.1 Grouping: 50 rats were randomly divided into 5 groups according to their body weights, 10 rats for each group:

(1) model group; (2) colchicine group (0.15 mg/kg); (3) B4 subcutaneous injection group (2.5 mg/kg*2); (4) B4 intramuscular injection group (2.5 mg/kg*2); (5) B4 intravenous injection group (2.5 mg/kg*2).

2.2.2 Administration: The model group was injected with the same volume of normal saline, and each test group (including B4 groups and colchicine group) was administered only on the day of model building. Among them, colchicine group was administered once, while each B4 group was successively administered two times with an interval of 4 h.

2.2.3 Model establishment and measurement of joint swelling: the model was initially established 1 h after administrating in the drug groups, and the method was same as that in example 1. Before modeling and 2 h, 4 h, 6 h, 8 h, and 12 h after modeling, the volume of the right ankle joint was measured, and the swelling degree was calculated by "joint volume after modeling joint volume before modeling".

3. Experimental results:

See Table 2.

The data in Table 2 showed that the swelling degree in the model group reached a peak 8 h-12 h after modeling. Compared with the model group, the joint swelling degree of each drug group was reduced to different degrees, wherein 6-12 h after modelling in B4 subcutaneous injection group, 8-12 h after modelling in B4 intramuscular injection group, and 8-12 h after modelling in B4 intravenous injection group, and 6-12 h after modelling in the colchicine group, the swelling degree of the joint was obviously reduced and significantly different compared with the model group. There was no significant difference between B4 groups and colchicine group, indicating that using the administration route and dosage in the experiment, the effect of B4 on reducing the joint swelling of acute gouty arthritis caused by sodium urate in rats was equivalent to that of colchicine. Although there was no significant difference, the joint swelling degree in B4 subcutaneous injection group was the smallest in all groups 2-8 h after modeling, while the joint swelling degree of B4 intramuscular injection group was the smallest in all groups 12 h after modeling, showing certain superior actions.

4. Experimental conclusions

The results of this experiment showed that similar to the results of Example 1, B4 injection has a significant effect on alleviating the joint swelling of acute gouty arthritis.

The invention claimed is:

1. A method for treatment of acute gouty arthritis, comprising administering a drug to a patient in need thereof, wherein the drug comprises anemoside B4, colchicine, one or more active ingredients selected from non-steroidal anti-inflammatory drugs and glucocorticoids, and a pharmaceutically acceptable excipient.

2. The method according to claim 1, wherein the drug is administered by subcutaneous injection, intramuscular injection, or intravenous infusion.

3. The method according to claim 1, wherein the patient is a human.

4. The method according to claim 1, wherein a dosage of anemoside B4 being administered is 0.4-1.6 mg/kg body weight of a patient at least one time a day.

5. The method according to claim 1, wherein anemoside B4 is administered to a person at a dosage of 0.4-1.6 mg/kg body weight at least one time a day by subcutaneous injection, intramuscular injection, or intravenous injection.

6. The method according to claim 1, wherein the non-steroidal anti-inflammatory drug is selected from one or

TABLE 1

Effect of B4 on the degree of joint swelling in rats with acute gouty arthritis induced by MSU ($\bar{x} \pm s$, n = 10).

| Groups | dose | Swelling degree | | | | | |
| --- | --- | --- | --- | --- | --- | --- | --- |
| | | 2 h after modelling | 4 h after modelling | 6 h after modelling | 8 h after modelling | 12 h after modelling | 24 h after modelling |
| Normal group | — | $0.05 \pm 0.03^{\Delta}$ | $-0.04 \pm 0.08^{\Delta}$ | $-0.05 \pm 0.07^{\Delta\Delta}$ | $-0.08 \pm 0.06^{\Delta\Delta}$ | $-0.13 \pm 0.07^{\Delta\Delta}$ | $-0.14 \pm 0.11^{\Delta\Delta}$ |
| Model group | — | $0.20 \pm 0.10$ | $0.25 \pm 0.10$ | $0.27 \pm 0.15$ | $0.36 \pm 0.19$ | $0.38 \pm 0.18$ | $0.31 \pm 0.14$ |
| B4 intravenous injection group | 5 mg/kg * 2 | $0.17 \pm 0.14$ | $0.08 \pm 0.18^{\Delta}$ | $0.13 \pm 0.14^{\Delta}$ | $0.23 \pm 0.21$ | $0.22 \pm 0.19$ | $0.28 \pm 0.21$ |
| B4 subcutaneous injection group | 5 mg/kg * 2 | $0.10 \pm 0.08^{\Delta}$ | $0.07 \pm 0.08^{\Delta\Delta}$ | $0.13 \pm 0.09^{\Delta}$ | $0.21 \pm 0.13$ | $0.27 \pm 0.15$ | $0.28 \pm 0.16$ |
| B4 intramuscular high-dose group | 5 mg/kg * 2 | $0.15 \pm 0.10$ | $0.15 \pm 0.09^{\Delta}$ | $0.19 \pm 0.11$ | $0.28 \pm 0.11$ | $0.33 \pm 0.16$ | $0.35 \pm 0.23$ |
| B4 intramuscular low-dose group | 2.5 mg/kg * 2 | $0.12 \pm 0.07^{\Delta}$ | $0.11 \pm 0.11^{\Delta}$ | $0.20 \pm 0.11$ | $0.32 \pm 0.18$ | $0.38 \pm 0.23$ | $0.55 \pm 0.35$ |
| Colchicine group | 0.3 mg/kg | $0.14 \pm 0.08$ | $0.13 \pm 0.11^{\Delta}$ | $0.19 \pm 0.14$ | $0.25 \pm 0.20$ | $0.35 \pm 0.23$ | $0.33 \pm 0.11$ |

Note:
Compared with the model group, $^{\Delta}P < 0.05$, $^{\Delta\Delta}P < 0.01$

TABLE 2

Effect of B4 on the degree of joint swelling in rats with acute gouty arthritis induced by MSU ($\bar{x} \pm s$, n = 10)

| Groups | Dose | Swelling degree | | | | |
| --- | --- | --- | --- | --- | --- | --- |
| | | 2 h after modelling | 4 h after modelling | 6 h after modelling | 8 h after modelling | 12 h after modelling |
| Model group | — | $0.141 \pm 0.06$ | $0.080 \pm 0.09$ | $0.151 \pm 0.11$ | $0.279 \pm 0.16$ | $0.279 \pm 0.15$ |
| Colchicine group | 0.15 mg/kg | $0.155 \pm 0.07$ | $0.082 \pm 0.11$ | $0.056 \pm 0.11^{\Delta}$ | $0.135 \pm 0.13^{\Delta}$ | $0.128 \pm 0.13^{\Delta}$ |
| B4 subcutaneous injection group | 2.5 mg/kg * twice | $0.067 \pm 0.10$ | $0.008 \pm 0.11$ | $0.040 \pm 0.09^{\Delta}$ | $0.103 \pm 0.18^{\Delta}$ | $0.103 \pm 0.16^{\Delta}$ |
| B4 intramuscular injection group | 2.5mg/kg * twice | $0.099 \pm 0.08$ | $0.130 \pm 0.07$ | $0.090 \pm 0.07$ | $0.134 \pm 0.10^{\Delta}$ | $0.097 \pm 0.17^{\Delta}$ |
| B4 intravenous injection group | 2.5mg/kg * twice | $0.113 \pm 0.09$ | $0.099 \pm 0.10$ | $0.108 \pm 0.18$ | $0.113 \pm 0.24^{\Delta}$ | $0.124 \pm 0.27^{\Delta}$ |

Note:
Compared with the model group, $^{\Delta}P < 0.05$, $^{\Delta\Delta}P < 0.01$.

more of ibuprofen, indomethacin, nimesulide, naproxen, nabumetone, diclofenac sodium, loxoprofen sodium, rofecoxib, celecoxib, and etoricoxib.

7. The method according to claim 1, wherein the glucocorticoid is selected from one or more of prednisone, meprednisone, betamethasone, beclomethasone dipropionate, diprospan, prednisolone, hydrocortisone, and dexamethasone.

8. The method according to claim 1, wherein the drug is an oral preparation.

9. The method according to claim 1, wherein the drug is a non-oral preparation selected from an injection, a preparation for rectal administration, and a preparation for pulmonary administration.

10. The method according to claim 9, wherein the drug is a injection selected from a subcutaneous injection, an intramuscular injection, and an intravenous infusion; and the preparation for rectal administration is a rectal suppository or a rectal infusion.

\* \* \* \* \*